US006107022A

United States Patent [19]

Suda et al.

[11] Patent Number: 6,107,022

[45] Date of Patent: Aug. 22, 2000

[54] HOP MOSAIC VIRUS GENE AND METHOD FOR DETECTING HOP MOSAIC VIRUS

[75] Inventors: Narushi Suda, Sorachi; Tatsuji Hataya, Sapporo, both of Japan

[73] Assignee: Sapporo Breweries Ltd., Tokyo, Japan

[21] Appl. No.: 09/120,887

[22] Filed: Jul. 23, 1998

[30] Foreign Application Priority Data

Jul. 23, 1997 [JP] Japan .................................... 9-212568

[51] Int. Cl.[7] .............................. C12Q 1/68; C12P 19/34; C07H 21/04

[52] U.S. Cl. .................................. 435/5; 435/6; 435/91.2; 536/23.1; 536/23.72; 536/24.32; 536/24.33

[58] Field of Search .................................. 435/5, 6, 91.2; 536/23.1, 23.72, 24.32, 24.33

[56] References Cited

FOREIGN PATENT DOCUMENTS

| | | |
|---|---|---|
| 0 775 747 | 5/1997 | European Pat. Off. . |
| 9 173100 | 7/1997 | Japan . |

OTHER PUBLICATIONS

Zavriev, S.K. GenBank Accession No. X53062, Sep. 1993.

Andrea Gramstat, et al., Febs Letters, vol. 276, No. 1 and 2, pp. 34–38, "The 12 kDa Protein of Potato Virus M Displays Properties of a Nucleic Acid–Binding Regulatory Protein", Dec. 10, 1990.

Y. Kanno, et al., Ann. Phytopath. Soc. Jap., vol. 59, 1 Page, "Some Properties of Hop Latent and Apple Mosaic Viruses Isolated From Hop Plants and Their Distributions in Japan", 1993, (Abstract only).

Derwent Abstracts, AN 95–018290, JP 06 304000, Nov. 1, 1994.

Derwent Abstracts, AN 95–018289, JP 06 303999, Nov. 1, 1994.

K. H. Ryu, Database EMBL., 1 page, "Cloning and Sequencing of LSV Korean Strain", Aug. 1997, (Abstract only).

Tatsuji Hataya et al, "Detection of Hop Latent Viroid (HLVd) Using Reverse Transcription and Polymerase Chain Reaction", Ann. Phytopath. Soc. Japan, vol. 58., pp. 677–684, Feb. 22, 1992.

E.G. Probasco et al, "A Technique for the Differential Isolation of Hop Mosaic Virus and Hop Latent Virus", Can. J. Microbiol., vol. 22., pp. 1160–1162, May 7, 1976.

A.N. Adams et al, "The Use of F(ab$^1$)$_2$—Based Elisa to Detect Serological Relationships Among Carlaviruses", Ann. appl. Biol., vol. 101., pp. 495–500, Jul. 29, 1982.

J. Yu et al, "The Occurrence of Three Viruses in Hop (Humulus Lupulus) in China", Plant Pathology, vol. 36., pp. 38–44, 1987.

Yoshiaki Kanno et al, "Some Properties of Hop Mosaic Virus Isolated in Japan", Ann. Phytopath. Soc. Japan, vol. 60., No. 6., pp. 675–680, Apr. 4, 1994.

A.N. Adams et al, "Host Range, Purification and Some Properties of Hop Mosaic Virus", Ann. appl. Biol., vol. 96., pp. 201–208, Jun. 11, 1980.

*Primary Examiner*—Carla J. Myers
*Attorney, Agent, or Firm*—Oblon, Spivak, McClelland, Maier Neustadt, P.C.

[57] ABSTRACT

The hop mosaic virus (HMV) gene has been isolated and purified, and the base sequence thereof elucidated. HMV can be detected by simple and accurate methods using nucleic sequences from the isolated HMV gene. These methods are especially useful for detecting HMV infection in plants. Using the methods provided by the present invention, it is possible to detect HMV more simply and accurately as compared to the conventional immunological methods, such as ELISA.

15 Claims, 2 Drawing Sheets

Results of the reverse transcription PCR using AP2, 3NTRAP2 and CARORF3 primers

M: DNA size markers (StyI digests of λDNA)

1. Potato virus S

2: Hop latent virus

3: Hop mosaic virus

4: Distilled Water

Results of the reverse transcription PCR using AP2, 3NTRAP2 and CARORF3 primers

M: DNA size markers (StyI digests of λDNA)

1: Potato virus S

2: Hop latent virus

3: Hop mosaic virus

4: Distilled Water

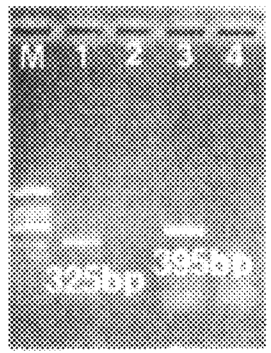

FIG. 2

M: DNA size markers ( HinfI digests of $\phi$x174)

1: HLV and HMV-positive hop by ELISA ( cultivar: Bullion/HLV gene diagnostic results)

2: HLV and HMV-negative hop by ELISA ( cultivar: Bullion/HLV gene diagnostic results)

3: HLV and HMV-positive hop by ELISA ( cultivar: Bullion/HMV gene diagnostic results)

4: HLV and HMV-negative hop by ELISA ( cultivar: Bullion/HMV gene diagnostic results)

HOP MOSAIC VIRUS GENE AND METHOD FOR DETECTING HOP MOSAIC VIRUS

BACKGROUND OF THE INVENTION

1. Field of the Invention

The present invention relates to the gene of the hop mosaic virus (abbreviated as HMV hereafter) and diagnostic methods for detecting HMV.

2. Description of the Background

HMV, a pathogenic virus of hop, is a filamentous shaped virus comprising a single stranded RNA genome and belongs to the same carlavirus group as the hop latent virus. HMV is an important causative pathogen of mosaic symptom to susceptible hop cultivars [Probasco and Skotland, Can. J. Microbiol. 22: 116011162 (1976); Adams and Barbara, Ann. Appl. Biol. 96: 201208 (1980); Adams and Barbara, Ann. Appl. Biol. 101: 495500 (1982); Yu and Liu, Plant Pathology 36: 3844 (1987); Kanno et al., Ann. Phytopath. Soc. Japan 680 (1994)]. Therefore, for the production of hop, surveys of fields which are not contaminated with this virus and inspections of virus-free seedlings are performed.

Conventionally, for the confirmation of virus-free seedlings and the field survey to prevent the viral reinfection immunodiagnostic methods such as ELISA have been employed. However, HMV diagnosis by ELISA poses various problems such as difficulties in the preparation as well as availability of antibodies. Furthermore, even though antibodies are available, ELISA still poses problems such as inferior accuracy of diagnostic results due to nonspecific reactions of the antibodies.

On the other hand, since gene sequences of various viruses have been elucidated owing to the recent progress in molecular biology, certain species of viruses can be accurately detected and diagnosed using genetic engineering techniques. However, the detection of HMV has relied upon the above-mentioned immunological procedure, because its gene sequences have not been elucidated.

Therefore, the present inventors have actively pursued efforts to isolate and purify the HMV gene and elucidate its base sequence. Furthermore, they have developed methods for detecting HMV using such nucleic acid sequences.

SUMMARY OF THE INVENTION

As described above, the present invention provides the gene of hop mosaic virus or nucleic acids comprising the partial sequence thereof, i.e., fragments of the HMV gene.

These isolated and purified (e.g., synthesized) nucleic acids allow the detection of the virus present within hop seedlings and in fields with by genetic procedures. For example, genetic procedures such as PCR, hybridization method, etc., using these nucleic acids enables the detection of minute quantity of the virus in a highly accurate manner.

The above described nucleic acids can be prepared from either the genomic RNA of hop mosaic virus or its corresponding cDNA.

The base sequence of the above described hop mosaic virus cDNA is actually the same as that from bases 1 to 1844 shown in SEQ. ID: NO. 1, or essentially the same sequence as this sequence. Herein, the term "essentially the same sequence" refers to a sequence which can be used to detect the hop mosaic virus with a genetic detection method such as a hybridization method, etc., including those hybridizable with the sequence of SEQ. ID. NO: 1. That is, such essentially the same sequences as that of SEQ. ID. NO. 1 can be prepared by a genetic procedure such as hybridization method, etc. using nucleic acids shown in the above described SEQ. ID. NO: 1. Preferably, such sequences are hybridizable under the conditions described herein below.

In addition, as the above described partial sequences, for example, the gene regions encoding the constituent of the viral particle, coat protein, etc., can be preferably used. More specifically, the sequence of SEQ. ID. NO: 1 encoding the 306 amino acid residues encoded by bases 525 to 1445 (SEQ ID NO: 3), the 102 amino acid residues encoded by bases 1445 to 1753 (SEQ ID NO: 4), or the 68 amino acid residues encoded by bases 302 to 508 (SEQ ID NO: 2) can be employed. Although for the use of these partial sequences may be employed the sequences in full length as described above, in the case wherein they are used as primers in PCR method or probes in hybridization method, regions comprising at least 15 bases and having appropriate length for the virus detection can be selected. For example, for the use as primers in PCR and probes in hybridization method base sequences shown in SEQ ID NOs 5 and 6 are preferably used. The present invention also includes any DNA sequence which encodes the 306 amino acid residues encoded by bases 525 to 1445 of SEQ ID NO: 1, the 102 amino acid residues encoded by bases 1445 to 1753 of SEQ ID NO: 1, or the 68 amino acid residues encoded by bases 302 to 508 of SEQ ID NO: 1.

Furthermore, the present invention provides a method for detecting the hop mosaic virus within hop samples to confirm whether they are contaminated with the virus by screening genetic procedures using the above-described purified nucleic acid.

According to the present invention, as compared with the conventional immunological technique, virus present in a minute quantity of sample can be detected in a high sensitivity. In the above-described genetic method, for example, the polymerase chain reaction (PCR) can be preferably used. That is, the infection with the hop mosaic virus can be speedily detected by amplifying the nucleic acid within the hop sample by PCR using a nucleic acid comprising a partial sequence of the hop mosaic virus gene as a primer, followed by measuring the length of the amplified product, i.e., detecting whether amplified nucleic acid from the hop mosaic virus gene was actually produced in the amplification. Of course, the presence of the amplified nucleic acid from the hop mosaic virus gene correlates with the presence of the virus in the hop sample tested, i.e., the hop tested is infected with the virus. Conversely, the lack of amplified nucleic acid from the hop mosaic virus gene correlates with the absence of the virus in the hop sample tested, i.e., the hop tested is not infected with the virus As the PCR primer described above, for example, nucleic acids of SEQ. ID. NOs: 2 or 6 can be preferably used. When they are used as primers, the infection with the hop mosaic virus can be detected by identifying a specific DNA fragment of 395 base pairs as the final amplified product. Primers can be designed not only by combining sequences in these SEQ. ID. NOs: 5 and 6 but also selecting appropriate regions from the sequence of SEQ. ID. NO: 1. In addition, sequences which are partially different from those in SEQ. ID. NOs. 1, 5 and 6 may be used as primers, so long as they can be annealed to the hop mosaic virus gene sequence and amplified.

As a genetic procedure other than PCR, a hybridization method may be preferably used. The probe used for this hybridization procedure can be prepared based on the hop mosaic virus gene or its partial sequence. For example, as this probe can be used the nucleic acid described in SEQ. ID. NO. 1, its complementary sequence, or partial sequences, i.e., fragments, thereof. As this partial sequence can be preferably used the nucleic acid of SEQ. ID. NO. 6. In addition, even nucleic acids which are partially different from that of SEQ. ID. NO. 1, but essentially the same as that of SEQ. ID. NO. 1 capable of hybridizing to the hop mosaic virus nucleic acid may be preferably used as the probe.

Furthermore, the present invention provides a kit for conveniently detecting the hop mosaic virus based on the above described nucleic acid and method. For example, in the case of detecting HMV by PCR, reagents necessary for PCR such as polymerase, etc. may be included therein in addition to the above described nucleic acid. Positive or negative control sample may be included therein if necessary. By providing such a kit, the detection of hop mosaic virus can be more conveniently carried out.

A more complete appreciation of the present invention and many of the attendant advantages thereof will be readily obtained as the same becomes better understood by reference to the following detailed description when considered in connection with the following drawings.

Figure 1:
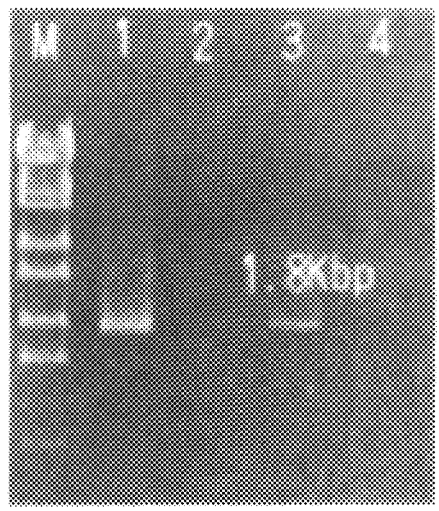
FIG. 1 is a photograph of an electrophoresis depicting the size of cDNA fragments of HMV gene as determined by reverse transcription PCR using AP2, 3NTRAP2 and CARORF3 primers.

Lane M: DNA size markers (StyI digests of λDNA)

Lane 1: Potato virus S

Lane 2: Hop latent virus

Lane 3: Hop mosaic virus

Lane 4: Distilled water.

FIG. 2 is a photograph depicting results of an electrophoresis of PCR products in the HMV gene diagnostic method of Example 5:

Lane M: DNA size markers (HinfI digests of ϕx174)

Lane 1: HLV and HMV-positive hop by ELISA (cultivar: Bullion/HLV gene diagnostic results)

Lane 2: HLV and HMV-negative hop by ELISA (cultivar: Bullion/HLV gene diagnostic results)

Lane 3: HLV and HMV-positive hop by ELISA (cultivar: Bullion/HMV gene diagnostic results)

Lane 4: HLV and HMV-negative hop by ELISA (cultivar: Bullion/HMV gene diagnostic results).

DETAILED DESCRIPTION OF THE PREFERRED EMBODIMENTS

1. Isolation and purification of HMV gene and determination of its base sequence 1) Concentration of HMV HMV can be concentrated from HMV-contaminated hop by standard methods, for example, the concentration using polyethylene glycol, clarification with organic solvent or heat treatment, fractional centrifugation, etc.

2) Extraction of RNA from the HMV concentrate

RNA extraction from the HMV concentrate may be carried out by standard methods such as SDS phenol method mainly used for the extraction from other plant viruses.

3) Cloning of cDNA

Utilizing the extracted RNA as a template, double-stranded cDNA is synthesized in vitro. For the synthesis of this double-stranded cDNA, it is effective to carry out the reverse transcription PCR using primers designed based on the base sequence of the same carlavirus group [Mackenzie et al., J. Gen. Virol.: 70, 10531063 (1989), Rupasov et al., J. Gen. Virol.: 70, 1861–1869 (1983), Foster et al., J. Gen. Virol.: 71, 1877–1880 (1990), Memelink et al., J. Gen. Virol.: 71, 917–924 (1990), Morozov et al., Virology: 183, 782–785 (1991), Levay & Zavriev, J. Gen. Virol.: 72, 2333–2337 (1991), Foster & Mills, Virus Gene: 6: 3, 213–220 (1992), Cavileer et al., J. Gen. Virol.: 75, 711–720 (1994); all of these references are incorporated herein by reference]. cDNA thus synthesized can be incorporated into a plasmid vector using standard techniques. As this plasmid can be used any ones such as pUC119, pBluescript II, etc. which are capable of autonomously replicating in *E. coli.*

After cloning, plasmid is inserted into the competent *E. coli* cells. After the cells inserted with the desired plasmid are selected, and grown in culture, plasmid are recovered from the transformed *E. coli* cells thus obtained, and purified by standard techniques. These procedures from cDNA cloning to plasmid recovery can be performed, for example, according to the method of Maniatis et al. (Cold Spring Harbor Laboratory Press, 1989, incorporated herein by reference).

4) Determination of base sequence of cDNA derived from the HMV genome

Using the above-described recombinant plasmid with the cloned cDNA insert, its base sequence may be determined according to either the Maxam-Gilbert method or the dideoxy method.

2. Viral gene diagnosis of the HMV infected hop

1) Viral gene diagnosis using reverse transcription PCR a) Synthesis of primers

Oligonucleotides are synthesized based on the base sequence of the HMV genome identified by the above described method or that of complementary strand of said base sequence and used as primers. These oligonucleotides used as primers in PCR are of at least 15 base length, preferably more than 17 bases in length, more preferably more than 20 bases in length. The primers may have a length up to, for example, 20, 25, 30, 35, 45 or 50 bases, inclusive of all specific values and subranges therebetween.

More specifically, primers comprising the base sequence of SEQ ID NOs 5 or 6 are preferably used. In addition, oligonucleotides which are not completely identical with those of SEQ ID NOs 5 and 6 but comprise partial sequence thereof may be used as primers. Since PCR is primarily to amplify the copy of a specific gene information selected out of many base sequences, even oligonucleotides comprising similar base sequences to that of the primer of the present invention are considered to be equally usable as the primer for the viral gene diagnosis.

Furthermore, the above described oligonucleotides can be obtained with a commercial automated DNA synthesizer using, for example, cyanoethylphosphoamidite method and thiophosphite methods.

b) Extraction of nucleic acid from hop samples

Nucleic acid can be extracted from hop plant by triturating and suspending sample tissues in a buffer for virus concentration followed by phenol treatment, etc. In addition, hop plant in any growth stage may be used as the above described hop sample.

c) Reverse transcription PCR

Using the nucleic acid thus obtained and the above described primer, DNA derived from the HMV genome is attempted by the reverse transcription PCR under the conditions using, for example, the method of Saiki et al. (Science, 230. 1350–1354, incorporated herein by reference).

More specifically, the PCR reaction solution can be prepared as follows. To an amplification buffer containing magnesium chloride (about 1.0 mM, preferably ranging from about 1.5 mM to about 3.0 mM), potassium chloride, gelatin, bovine serum albumin, surface active agent (Tween 20, NP-40, Triton X-100, etc.), dimethyl sulfoxide, etc. are added two different oligonucleotides, DNA polymerase, four bases (dATP, dTTP, dCTP and dGTP) and DNA extracted from hop sample. In addition, thermostable DNA polymerase is exemplified by the one available from PERKIN ELMER.

In the PCR reaction, the following cyclic process is repeated 20~50 times, preferably 25~40 times. The denaturation step is performed by heating the reaction mixture generally at from 90° C. to 95° C., preferably at from about 94° C. to 95° C. for about 30 s to 2 min, preferably for about 30 s to 2 min. The primer annealing step is carried out by incubating with primers generally at from 30° C. to 60° C., preferably at from about 30° C. to 55° C. for about 1 min to about 3 min, preferably for about 1 min to 2 min. The elongation step with DNA polymerase is carried out by the treatment with a thermostable DNA polymerase generally at from about 70° C. to about 73° C., preferably at from 72° C. to 73° C. for about 30 s to about 4 min, preferably for about 30 s to about 2 min.

Amplified DNAs obtained by the above described PCR are fractionated by electrophoresis on agarose gel, acrylamide gel, etc., selected according to the size of DNA. In the case of agarose gel, it can be used generally at the concentration of about 0.5% to about 3%. The electrophoretic buffer is exemplified by Tris-phosphate (pH 7.5~pH 8.0), Tris-acetate (pH 7.5~pH 8.0), Tris-borate (pH 7.5~pH 8.3) systems, etc., preferably Tris-borate. EDTA, etc., may be added therein if necessary.

Electrophoresis is carried out under the conditions, for example, at 50 V to 300 V for 10 min to 120 min, preferably at 150 V for 30 min, and, as size markers may be used, for example, a commercial 100 Base-Pair Ladder (Pharmacia, Inc.). After electrophoresis, amplified DNAs thus fractionated can be visualized for detection by the staining method using dyes of phenanthridine series such as ethidium bromide which can interact with nucleic acids. Said staining dye may be added not only after electrophoresis, but also prior to it into the electrophoretic buffer. In the case of staining after the termination of electrophoresis, the gel is immersed in a solution of ethidium bromide, etc. for about 60 min, and irradiated with ultraviolet light at 254 nm or 366 nm in the dark to detect red bands. Alternatively, in the case of staining during electrophoresis, dye such as ethidium bromide is added to the electrophoretic buffer at a final concentration of about 0.5 g/ml. In such a case of staining simultaneously performed with electrophoresis, red bands can be detected by irradiating the gel with UV at 254 nm or 366 nm in the dark even during electrophoresis.

The virus infection can be detected from the presence or absence of amplified DNAs. That is, when PCR is carried out using the same primer, the specific amplified DNA is detected with samples derived from the virus infected hop, but not with those from the uninfected hop.

For example, when the base sequences of the above described SEQ ID NOs 5 and 6 are used as primer, a specific DNA segment comprising 395 base pairs is amplified with samples from the virus infected hop. However, in the case of transformed HMV, said specific DNA segment may vary in its length.

(2) Gene diagnosis by hybridization

An HMV diagnosis different from the conventional immunoassay can be performed by preparing nucleic acids having the sequence complementary to that of the HMV genomic DNA either by chemical synthesis or gene manipulation, and hybridizing with said nucleic acids as probe.

As probes are used nucleic acids with the chain length of generally 20 to several thousands bases, exemplified by DNA fragments produced by cleaving cDNA of said HMV genome with restriction enzymes. Prior to hybridization, these probes are modified either at the terminus or internally with radiation emitters such as radioisotope, fluorescer, etc., secondarily labelable substances such as biotin, digoxigenin, etc., enzymes such as alkaline phosphatase, etc. by standard methods.

The hop plant nucleic acids used for hybridization can be extracted standard methods, for example, the standard nucleic acid extraction method described in Murray & Thompson, Nucl. Acid Res., 8, 4321–4325 (1980), incorporated herein by reference. Nucleic acids thus obtained are subjected to the denaturation treatment, and then spotted on a membrane filter, such as nitrocellulose filter or nylon filter, preferably, for example, Hybond-N+ (Amersham).

The denaturation treatment of nucleic acids are carried out by heating them in a solution containing formamide, MOPS, sodium acetate, EDTA, etc. at 60~70° C., preferably at 65° C. for 5~20 min, preferably for 15 min, followed by quick cooling. After this denaturation treatment, nucleic acids are mixed with 20×SSC, and then spotted on membrane filter.

Nucleic acids spotted on membrane filter are hybridized with the above described probes in a hybridization solution under conditions at 42~65° C., preferably at 46° C. for 12~20 h, preferably for 16 h. After the reaction, the membrane filter is rinsed, dried and inspected for the presence or absence of the signal at spots by the detection method such as autoradiography, etc. That is, the signal is detected with nucleic acids (DNA+RNA) derived from the virus infected hop because of their hybridization with probe, but not detected with those derived from uninfected hop because of their lack in the complementary sequences to probe.

3. Application of synthesized nucleic acids of the HMV gene

Synthesized nucleic acids of HMV gene can be applied not only for the above described method for detecting HMV virus, but also for the creation of hop resistant to the present virus using antisense techniques. More specifically, HMV gene is inserted to an expression vector in such a manner to allow the formation of the antisense RNA, and transform hop with said vector resulting in the production of transformed hop showing the resistance to the virus.

EXAMPLES

In the following Examples, the present invention will be described in more detail with reference to examples, which are designed to illustrate, but not limit, the present invention.

Example 1

Concentration of HMV

Seedling stems of the HMV-infected hop (cultivar: Bullion, single infection with HMV has been confirmed by ELISA) (100 g) were ground in 4 volumes of 0.5 M potassium phosphate buffer, pH 7.2, (containing 1% sodium sulfite) and filtered through gauze to obtain the crude extract.

Then Triton X-100 (8 ml) was added to said extract, and, after the mixture was stirred for 1 h, it was centrifuged at 3,000×g for 10 min to obtain the supernatant. To this supernatant was added ⅓ volume of carbon tetrachloride, and the mixture was stirred in the ice-cold for 3 min, and centrifuged at 3,000×g for 10 min to obtain the supernatant again. To the supernatant thus obtained was added polyethylene glycol (20 g) and sodium chloride (2.4 g), the mixture was stirred for 40 min, left standing for 1 h, and then centrifuged at 3,000×g for 40 min to obtain precipitates. The precipitates were suspended in 0.5 M potassium phosphate buffer, pH 7.2 (containing 1% Triton X-100), centrifuged at high speed (15,000×g for 10 min) to obtain the supernatant, which was further ultracentrifuged (at 100,000×g for 120 min) to recover precipitates. This fractional centrifugation process was repeated twice to isolate the virus free from contaminant, suspended in 0.5 M potassium phosphate buffer, pH 7.2, and stored as the HMV concentrate.

Except where otherwise stated, all the procedures described above were carried out 4° C.

Example 2

Extraction of RNA from HMV

Extraction of RNA from the HMV concentrate was performed by the SDS phenol method [Proll et al., Potato Research 24, 110 (1981), incorporated herein by reference].

To an HMV concentrated solution (178 $\mu$l) obtained by a similar method as in Example 1 were added 20% SDS (10 $\mu$l), 20×SSC (2 $\mu$l) and protease (20 mg/ml) (10 $\mu$l), and the resulting mixture was warmed at 37° C. for 30 min. Phenol extraction was then performed by adding 0.5% bentonite suspension (100 $\mu$l) and a TE-saturated phenol (300 $\mu$l) to the above mixture followed by the second phenol extraction using an equal volume of a mixture of phenol:chloroform (1:1, v/v). After the aqueous layer was extracted with chloroform, to the aqueous layer were added 3 M sodium acetate (10 $\mu$l) and cold ethanol (250 $\mu$l), and the resulting mixture was left standing at −80° C. for 30 min. The mixture was then centrifuged at 15,000×g for 5 min to obtain precipitates, which were washed by centrifugation in 70% ethanol. After removing the ethanol by drying, the precipitates thus obtained were dissolved in distilled water (100 $\mu$l). To this solution was added 4 M lithium chloride (100 $\mu$l), and the mixture was left standing in an ice bath overnight.

Then the above mixture was centrifuged at 15,000×g for 5 min to obtain precipitates, which were washed again by centrifugation in 70% ethanol as above. After the removal of ethanol by drying, the precipitates were dissolved in distilled water (20 $\mu$l) and stored as the RNA sample.

Example 3

Cloning of cDNA

Initially, based on the base sequence of Calravirus belonging to the same group as HMV, CARORF primer (5'TGCCACTTACACCGCCTCCT3') (SEQ ID NO 7), AP2 primer (5'-GCTACCATGGACGTCCGCGCGG(T)15-3') (SEQ ID NO 8), wherein an adaptor was linked to oligo-dT, and 3NTRAP 2 primer (5'-CGATGGTACCTGCAGGCGCGCC-3') (SEQ ID NO 9), which is complementary to the sequence of said AP 2 primer, were synthesized. To the RNA sample (3 $\mu$l) were added 10 $\mu$M AP2 primer (1. $\mu$l) and distilled water (7 $\mu$l), and the mixture was left at standing at 65° C. for 10 min. Then, RNA was denatured by quick cooling, mixed with 5×reverse transcriptase buffer (GIBCO BRL) (4 $\mu$l), 2.5 mM dNTP (1 $\mu$l) and reverse transcriptase (2,000 U/$\mu$l, GIBCO BRL) (1 $\mu$l), and the reverse transcription reaction was carried out at 42° C. for 1 h.

In order to perform PCR, the reaction solution comprising 10×PCR buffer (Boehringer) (5 $\mu$l), 2.5 mM dNTP (4 $\mu$l), 10 $\mu$M 3NTRAP2 primer (1 $\mu$l), 10 $\mu$M CARORF3 primer (1 $\mu$l), thermostable DNA polymerase (5 U/$\mu$l, Boehringer) (1 $\mu$l) and distilled water (33 $\mu$l) was prepared. Reaction conditions were as follows: each cycle comprises the denaturation step (98° C., 30 s) and elongation step (68° C., 5 min), and this cycle was repeated 30 times. One/tenth amount of amplified products was subjected to electrophoresis on 1.0% agarose gel (in 1×TRE buffer), and the amplified DNA segment of about 1.8 Kb was identified (FIG. 1).

Then, the above described amplified PCR product was blunt ended, and connected to the SmaI restriction enzyme site of pUC119. More specifically, the plasmid pUC119 was digested with SmaI to prepare segments, which were further dephosphorylated (50 ng/$\mu$l) (2 $\mu$l), and mixed with the blunt ended PCR product (1 $\mu$l). Next, to this mixture were added 10 mM ATP, 10×ligation buffer (Boehringer), T4 DNA ligase (5 U/$\mu$l, Boehringer) and distilled water (13 $\mu$l), and the resulting mixture was kept warm at 22° C. overnight to facilitate out the ligation reaction.

Competent cells of *Esherichia coli* MV1184 (100 $\mu$l) were prepared, mixed with the above-described ligation reaction solution, and the mixture was left at standing on ice for 30 min, warmed below 42° C. for 60 s, and then quickly cooled in ice. To this cell solution was added SOC medium (500 $\mu$l), and the resulting mixture was warmed at 37° C. for 1 h, evenly inoculated on agar medium, and incubated at 37° C. overnight. The agar medium used herein was prepared by adding 2% X-gal (50 $\mu$l), 100 mM IPTG (50 $\mu$l) and ampicillin (50 g/ml) to 2×YT agar medium.

After incubation overnight, plural white colonies (Lac Z-) were selected, inoculated respectively to the liquid medium, and incubated. From these culture solutions were extracted the plasmid DNA by standard methods. *E. coli* cells having the plasmid with cDNA fragment (about 1.8 Kb) derived from HMV genome inserted were selected, and stored.

Example 4

Determination of the Base Sequence of cDNA Derived From the HMV Genome

*E. coli* cells selected in Example 3 were shake-cultured in 2×YT medium at 37° C. overnight, and plasmids were prepared by standard methods. With the above-described cDNA fragments as template, they were decoded for their base sequence by the dideoxy method [Sanger et al., Proc. Natl. Acad. Aci., 74, 5463 (1977), incorporated herein by reference] using a DNA sequencer (Li-Cor, Inc.) and a sequence kit (Amersham) to determine the sequence of 1844 bases. These results are shown in SEQ ID NO: 1.

From the base sequence thus obtained, the translation regions were analyzed. As a result, out of said base sequence, the translation region (the sequence from bases 302 to 508 of SEQ ID NO 1 in the sequence listing) encoding a protein having the molecular weight about 6.9 kD (68 amino acid residues), that (the sequence from bases 525 to 1445 of SEQ ID NO 1 in the sequence listing) putatively encoding a capsid protein (306 amino acid residues, the molecular weight 33.9 kD), and that (the sequence from bases 1445 to 1753 of SEQ ID NO 1 in the sequence listing) encoding a protein having the molecular weight about 11.3 kD (102 amino acid residues) were identified.

Example 5

Gene Diagnosis of the HMV-Infected Hop by Reverse Transcription PCR

Leaves of the HMV-infected hop (cultivar, Bullion) or the virus-free hop (the same cultivar) (0.1 g each) were triturated in 0.5 M potassium phosphate buffer (pH 7.2, 1 ml), respectively, and the triturate solution was extracted with chloroform. After the supernatant thus obtained was treated with phenol and then with ether three times, ethanol was added thereto to precipitate nucleic acids. The precipitates thus obtained were washed by centrifugation in 70% ethanol, and the remaining ethanol was removed by drying. Dried nucleic acids were dissolved in distilled water (50 l), and a 2-l aliquot was subjected to the reverse transcription PCR.

Primers used for PCR were designed based on the present base sequence, and synthesized by standard methods using a DNA synthesizer (ABI, Model 380B). Sequences of primers synthesized herein are shown in SEQ ID NOs 5 and 6, hereafter abbreviated as lP and lM, respectively.

Using these primers, the reverse transcription reaction was performed. First, lM primer (25 pM), reverse transcriptase (Nippon Gene, 5 U), and the hop nucleic acids prepared above (2 μg) were mixed. To this mixture was added 50 mM Tris-HCl buffer (pH 8.3) (containing 75 mM KCl, 3 mM MgCl2, 10 mM DDT and 0.5 mM dNTP), and the resulting mixture was incubated at 37° C. for 1 h.

Then, to the reverse transcription products were added a thermostable DNA polymerase (Boehringer, 0.5 U) and the primer for amplification (25 pM) to perform PCR. The volume of the reaction solution was set to be 10 μl, and mineral oil (about 20 μl) was layered on top to prevent the evaporation of the reaction solution.

Each step in PCR was performed under the following conditions. After maintaining PCR mixture at 94° C. for 3 min, PCR cycle comprising the denaturation step at 94° C. for 1 min, the primer annealing step at 55° C. for 1 min, and the DNA elongation step at 72° C. for 2 min was repeated 30 times. Then the reaction solution was kept at 72° C. for 5 min, and stored at 4° C.

Amplified DNAs obtained by the above described PCR were analyzed for the size by electrophoresis, which was carried out on 2% agarose gel in Tris-borate buffer (pH 8.0) containing 2 mM EDTA at 100 V for 30 min. As size markers were used x174 DNA digests by the restriction enzyme HinfI (Nippon Gene).

After the completion of electrophoresis, gel was immersed in aqueous solution of ethidium bromide (0.5 g/ml) for 10 min, and irradiated with UV 254 nm in the dark to detect red bands of DNA-ethidium bromide complex. Fractionation patterns obtained by electrophoresis were shown in FIG. 2.

As the result of agarose gel electrophoresis, a specific DNA amplified fragment (395 bp) was obtained from the HMV-infected hop corresponding to the primer used, but not from the uninfected hop, allowing the differentiation between the two.

Example 6

Gene Diagnosis by Dot Blot Hybridization

Samples subjected to the dot blot hybridization were prepared by the following procedures.

Leaves of HMV-infected hop and virus-free hop (0.1 g each) were triturated in 0.5 M potassium phosphate buffer (pH 7.2, 1 ml), and the triturate solution was extracted with chloroform. After the supernatant thus obtained was further treated with phenol and then with ether three times, ethanol was added thereto to precipitate nucleic acids. The precipitates thus obtained were washed by centrifugation in 70% ethanol, and the remaining ethanol was removed by drying. Dried nucleic acids were dissolved in TE buffer (20 μl).

To a 2-μl aliquot of said solution was added three volumes of the nucleic acid denaturing buffer (consisting of 65% formamide, 20% formaldehyde, 1.54 M MOPS, 6.5 mM sodium acetate and 1.3 mM EDTA), and the mixture was warmed at 65° C. for 15 min, and then quickly cooled. To this solution was added 20×SSC (consisting of 0.15 M sodium chloride and 0.015 M sodium citrate at pH 7.0). A 10-μl aliquot of the resulting mixture was spotted on a membrane filter (Amersham, trade name: Hybond-N+) and subjected to the dot hybridization.

Probes were formed by digesting *E. coli*-derived plasmids prepared in Example 4 with the restriction enzymes BamHI and EcoRI and purifying the digests. This purification was performed by isolating digvested fragments with agarose gel and eluting the HMV-derived cDNA using a column (Takarashuzo, trade name: Suprec01 TM column).

Then, the cDNA thus eluted was labelled with [α-$^{32}$P] dCTP using a random labelling kit (Takarashuzo) and passed through a Sephadex G50 column to remove unbound [α32P] dCTP.

Hybridization was performed in a solution containing 5×SSC, 100 μg/ml yeast tRNA (Boehringer), 0.5% SDS, 0.1% Ficoll, 0.1% PVP and 0.1% BSA at 46° C. for 16 h. As a result of an autoradiogram, signals were observed at spots derived from HMV-infected hop, but not from HMV-free hop.

From results described above, it has been confirmed that HMV-infected hop can be differentiated from HMV-free hop according to the presence or absence of said signal.

As described above, in the present invention, not only the gene structure of HMV genome from 3'-terminus to the base 1844 has been elucidated, but also a HMV gene diagnostic method has been developed, enabling providing a highly accurate detection method for HMV. In the genetic detection method of the present invention, plural detection procedures required in the conventional immunological method, including the isolation of HMV, preparation of antisera, purification of antibodies, become unnecessary, allowing a more speedy detection of HMV. Furthermore, the genetic detection method of the present invention enables the diagnosis of HMV infection with a higher accuracy and precision than the conventional ELISA. In addition, the present invention enables the contribution, for example, to the creation of hop resistant to the present virus by transforming hop with the antisense strand of this gene.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Hei 9-212568, filed Jul. 23, 1997, and incorporated herein by reference in its entirety.

What is claimed is:

1. A nucleic acid consisting of SEQ ID NO: 1,2 or 3.

2. The nucleic acid of claim 1, which consists of SEQ ID NO: 1.

3. The nucleic acid of claim 1, which consists of SEQ ID NO: 2.

4. The nucleic acid of claim 1, which consists of SEQ ID NO: 3.

5. A method of assaying for the presence of hop mosaic virus in a hop sample, comprising:

treating (a) an isolated and purified nucleic acid consisting of SEQ ID NO: 1, 2 or 3 with a sample containing (b) nucleic acid obtained from hop; and detecting the presence or absence of hybridization between (a) and (b), wherein the presence of hybridization between (a) and (b) is indicative of the presence of hop mosaic virus in the hop sample, and the absence of hybridization between (a) and (b) is indicative of the absence of hop mosaic virus in the hop sample.

6. The method of claim 5, wherein (a) consists of SEQ ID NO: 1.

7. The method of claim 5, wherein (a) consists of SEQ ID NO: 2.

8. The method of claim 5, wherein (a) consists of SEQ ID NO: 3.

9. A method of assaying for the presence of hop mosaic virus in a hop sample, comprising:

treating (a) an isolated and purified nucleic acid comprising SEQ ID NO: 2 or 3 with a sample containing (b) nucleic acid obtained from hop in a polymerase chain reaction (PCR) to produce amplification products, detecting the presence or absence of the amplification products, wherein the presence of the amplification products is indicative of the presence of hop mosaic virus in the hop sample, and the absence of the amplification products is indicative of the absence of hop mosaic virus in the hop sample.

10. The method of claim 9, wherein (a) comprises SEQ ID NO: 2.

11. The method of claim 9, wherein (a) comprises SEQ ID NO: 3.

12. The method of claim 9, wherein (a) consists of SEQ ID NO: 2.

13. The method of claim 9, wherein (a) consists of SEQ ID NO: 3.

14. An isolated and purified nucleic acid fragment encoding a coat protein of hop mosaic virus.

15. An isolated and purified nucleic acid fragment which (1) specifically hybridizes to a nucleic acid encoding a coat protein of hop mosaic virus and (2) has a length of at least 15 nucleotides.

* * * * *

SEQUENCE LISTING

```
<160> NUMBER OF SEQ ID NOS: 9

<210> SEQ ID NO 1
<211> LENGTH: 1844
<212> TYPE: DNA
<213> ORGANISM: Hop Mosaic Virus
<220> FEATURE:
<221> NAME/KEY: CDS
<222> LOCATION: (302)..(508)
<220> FEATURE:
<221> NAME/KEY: CDS
<222> LOCATION: (525)..(1445)
<220> FEATURE:
<221> NAME/KEY: CDS
<222> LOCATION: (1445)..(1753)

<400> SEQUENCE: 1

cgcctgatta caccaaagtt ttggctagtg ctgtgatcgg ggctacgtta gcactcatca      60

cgtggacctt gagtaggaac acattgccac aagttgggga tagggatcat tatctgccgc     120

acgggggttt ctatagggac ggtacgaaag ttattcgcta ctttgggccg aataagctaa     180

attccctgga aggtagatct ggtggagggc tctggcagcc ttgggccata gtcgtggtgc     240

tggtagcagt tatagttgga ctcagcaagg gtttctaccc acggtgcgct aggtgtggcc     300

a atg tca tta aat ctg gtc tgc gcc tgt gtc ggg tta gtt tgc ttc gct     349
  Met Ser Leu Asn Leu Val Cys Ala Cys Val Gly Leu Val Cys Phe Ala
    1               5                  10                  15

tgc att ttg gtg tac ctg agt ggt gga ggc aat agc tgt ata gtt gtc       397
Cys Ile Leu Val Tyr Leu Ser Gly Gly Gly Asn Ser Cys Ile Val Val
             20                  25                  30

cta acg ggg gaa tca gtt agg ttc caa ggt tgc gac gtc aca gaa gag       445
Leu Thr Gly Glu Ser Val Arg Phe Gln Gly Cys Asp Val Thr Glu Glu
         35                  40                  45

ttc gcg cgt gcc tta tca aac gtc aag tcc ctt ggg ggt tgt ggt act       493
Phe Ala Arg Ala Leu Ser Asn Val Lys Ser Leu Gly Gly Cys Gly Thr
     50                  55                  60

tta ggt tta gag tga ataattgatc aaaata atg tct ggg agt act gaa gca     545
Leu Gly Leu Glu                       Met Ser Gly Ser Thr Glu Ala
 65                                    70                  75

gga aag ctt gcc cct gag gcc cag aaa ccg cag tat ggt ggg gaa gaa       593
Gly Lys Leu Ala Pro Glu Ala Gln Lys Pro Gln Tyr Gly Gly Glu Glu
             80                  85                  90

acc aag ctc aag gag aaa gtg ggg gct ggc gag tcc tca acc gta agt       641
Thr Lys Leu Lys Glu Lys Val Gly Ala Gly Glu Ser Ser Thr Val Ser
         95                 100                 105

gta gat gat tac gct gcc ggg ctt aaa gat ctg gag gcg gtc cgg gag       689
Val Asp Asp Tyr Ala Ala Gly Leu Lys Asp Leu Glu Ala Val Arg Glu
    110                 115                 120

gaa atg cta gaa gcg aga ttg gag aag ctg agg gaa ttt atg cgc agc       737
Glu Met Leu Glu Ala Arg Leu Glu Lys Leu Arg Glu Phe Met Arg Ser
125                 130                 135                 140

ggc gca gtg ctg ttc aat cac gaa ttc tgg ctt gga act ggt agg ccg       785
Gly Ala Val Leu Phe Asn His Glu Phe Trp Leu Gly Thr Gly Arg Pro
                145                 150                 155

gct ttg aca ctt act gct gat atg cgc tcc gac cca gcc aac cct tac       833
Ala Leu Thr Leu Thr Ala Asp Met Arg Ser Asp Pro Ala Asn Pro Tyr
            160                 165                 170

tgt aaa cca tct ctt gac tca ctg ctg cgt ata cca ccg aaa cct gtt       881
Cys Lys Pro Ser Leu Asp Ser Leu Leu Arg Ile Pro Pro Lys Pro Val
        175                 180                 185
```

-continued

```
tcc aat aat atg gct acc gca gag gac ata atg aaa atc tat aca aac      929
Ser Asn Asn Met Ala Thr Ala Glu Asp Ile Met Lys Ile Tyr Thr Asn
    190                 195                 200

ttg gag ggg cta ggt gta ccg act gag cac ata caa agg gta atc att      977
Leu Glu Gly Leu Gly Val Pro Thr Glu His Ile Gln Arg Val Ile Ile
205                 210                 215                 220

cag gca gtg ata tat tgt aag gat gcg agc agc tct gta tat cta gat     1025
Gln Ala Val Ile Tyr Cys Lys Asp Ala Ser Ser Ser Val Tyr Leu Asp
                225                 230                 235

cca agg ggc tct ttt gag tgg cct ggc gga gcc att gca gct gac tca     1073
Pro Arg Gly Ser Phe Glu Trp Pro Gly Gly Ala Ile Ala Ala Asp Ser
            240                 245                 250

gta ctg gcc att atg aag aag gac gca gaa aca cct cgg agg gtc tgc     1121
Val Leu Ala Ile Met Lys Lys Asp Ala Glu Thr Pro Arg Arg Val Cys
        255                 260                 265

cga ttg tat gca ccc gtg acg tgg tct tac atg ttg gtg cac aac cag     1169
Arg Leu Tyr Ala Pro Val Thr Trp Ser Tyr Met Leu Val His Asn Gln
    270                 275                 280

cca ccc tct gac tgg gcg gcc atg ggg ttt caa ttc gag gat cgc ttt     1217
Pro Pro Ser Asp Trp Ala Ala Met Gly Phe Gln Phe Glu Asp Arg Phe
285                 290                 295                 300

gct gcc ttc gac tgc ttc gat tat gtt gag aat gca gct gcc gta caa     1265
Ala Ala Phe Asp Cys Phe Asp Tyr Val Glu Asn Ala Ala Ala Val Gln
                305                 310                 315

ccg ctt gaa ggc att gta agg cga cca act cca agg gag aag ctg gcg     1313
Pro Leu Glu Gly Ile Val Arg Arg Pro Thr Pro Arg Glu Lys Leu Ala
            320                 325                 330

cac aac aca cac aaa gat atg gcc ctt cga aaa gcc aat agg aat cag     1361
His Asn Thr His Lys Asp Met Ala Leu Arg Lys Ala Asn Arg Asn Gln
        335                 340                 345

cat ttt ggg aat atg gac gtg gag gtc acc ggc ggc cgc agt ggc cca     1409
His Phe Gly Asn Met Asp Val Glu Val Thr Gly Gly Arg Ser Gly Pro
    350                 355                 360

gag att atc cgt gat tat tcc aag tcg aat agg ta atg atg cac tgg      1456
Glu Ile Ile Arg Asp Tyr Ser Lys Ser Asn Arg    Met Met His Trp
365                 370                 375

tgg cgt gct gct atg tta tta tat aaa gtt atg ttt gat gtg tgt ggt     1504
Trp Arg Ala Ala Met Leu Leu Tyr Lys Val Met Phe Asp Val Cys Gly
380                 385                 390                 395

agg tct agt ctt tac att agc gtt gat ata gct cgg agg gcg ggc cgt     1552
Arg Ser Ser Leu Tyr Ile Ser Val Asp Ile Ala Arg Arg Ala Gly Arg
                400                 405                 410

cct att ggg ggc ggt aag tcg tcc tat gct cgt aag aga cgc gca ata     1600
Pro Ile Gly Gly Gly Lys Ser Ser Tyr Ala Arg Lys Arg Arg Ala Ile
            415                 420                 425

aag atg ggg cga tgt gtg cgg tgc tac cgc gtc tca ccg cct ttc tat     1648
Lys Met Gly Arg Cys Val Arg Cys Tyr Arg Val Ser Pro Pro Phe Tyr
        430                 435                 440

cat act act aga tgt gac ggt ttg tcg tgt gta cct gga ctc tcg cta     1696
His Thr Thr Arg Cys Asp Gly Leu Ser Cys Val Pro Gly Leu Ser Leu
    445                 450                 455

aat gct ggc gtc gcc agg tta atc aag ggt gga gta act gag gtg atc     1744
Asn Ala Gly Val Ala Arg Leu Ile Lys Gly Gly Val Thr Glu Val Ile
460                 465                 470                 475

cca tcc tag tccaaatgaa gcgagagtag ccactaaatc ctatttaata             1793
Pro Ser

tataaggtgt gctactataa ataaaatttg gtttttaaat atttttagcc a            1844

<210> SEQ ID NO 2
```

-continued

```
<211> LENGTH: 68
<212> TYPE: PRT
<213> ORGANISM: Hop Mosaic Virus

<400> SEQUENCE: 2

Met Ser Leu Asn Leu Val Cys Ala Cys Val Gly Leu Val Cys Phe Ala
  1               5                  10                  15

Cys Ile Leu Val Tyr Leu Ser Gly Gly Gly Asn Ser Cys Ile Val Val
             20                  25                  30

Leu Thr Gly Glu Ser Val Arg Phe Gln Gly Cys Asp Val Thr Glu Glu
         35                  40                  45

Phe Ala Arg Ala Leu Ser Asn Val Lys Ser Leu Gly Gly Cys Gly Thr
     50                  55                  60

Leu Gly Leu Glu
 65


<210> SEQ ID NO 3
<211> LENGTH: 306
<212> TYPE: PRT
<213> ORGANISM: Hop Mosaic Virus

<400> SEQUENCE: 3

Met Ser Gly Ser Thr Glu Ala Gly Lys Leu Ala Pro Glu Ala
  1               5                  10

Gln Lys Pro Gln Tyr Gly Gly Glu Glu Thr Lys Leu Lys Glu Lys Val
15                  20                  25                  30

Gly Ala Gly Glu Ser Ser Thr Val Ser Val Asp Asp Tyr Ala Ala Gly
          35                  40                  45

Leu Lys Asp Leu Glu Ala Val Arg Glu Glu Met Leu Glu Ala Arg Leu
      50                  55                  60

Glu Lys Leu Arg Glu Phe Met Arg Ser Gly Ala Val Leu Phe Asn His
  65                  70                  75

Glu Phe Trp Leu Gly Thr Gly Arg Pro Ala Leu Thr Leu Thr Ala Asp
80                  85                  90

Met Arg Ser Asp Pro Ala Asn Pro Tyr Cys Lys Pro Ser Leu Asp Ser
95                  100                 105                 110

Leu Leu Arg Ile Pro Pro Lys Pro Val Ser Asn Asn Met Ala Thr Ala
          115                 120                 125

Glu Asp Ile Met Lys Ile Tyr Thr Asn Leu Glu Gly Leu Gly Val Pro
      130                 135                 140

Thr Glu His Ile Gln Arg Val Ile Ile Gln Ala Val Ile Tyr Cys Lys
  145                 150                 155

Asp Ala Ser Ser Ser Val Tyr Leu Asp Pro Arg Gly Ser Phe Glu Trp
160                 165                 170

Pro Gly Gly Ala Ile Ala Ala Asp Ser Val Leu Ala Ile Met Lys Lys
175                 180                 185                 190

Asp Ala Glu Thr Pro Arg Arg Val Cys Arg Leu Tyr Ala Pro Val Thr
          195                 200                 205

Trp Ser Tyr Met Leu Val His Asn Gln Pro Pro Ser Asp Trp Ala Ala
      210                 215                 220

Met Gly Phe Gln Phe Glu Asp Arg Phe Ala Ala Phe Asp Cys Phe Asp
  225                 230                 235

Tyr Val Glu Asn Ala Ala Ala Val Gln Pro Leu Glu Gly Ile Val Arg
240                 245                 250

Arg Pro Thr Pro Arg Glu Lys Leu Ala His Asn Thr His Lys Asp Met
255                 260                 265                 270
```

-continued

```
Ala Leu Arg Lys Ala Asn Arg Asn Gln His Phe Gly Asn Met Asp Val
          275                 280                 285

Glu Val Thr Gly Gly Arg Ser Gly Pro Glu Ile Ile Arg Asp Tyr Ser
      290                 295                 300

Lys Ser Asn Arg
  305


<210> SEQ ID NO 4
<211> LENGTH: 102
<212> TYPE: PRT
<213> ORGANISM: Hop Mosaic Virus

<400> SEQUENCE: 4

Met Met His Trp Trp Arg Ala Ala Met Leu Leu Tyr Lys Val Met Phe
  1               5                  10                  15

Asp Val Cys Gly Arg Ser Ser Leu Tyr Ile Ser Val Asp Ile Ala Arg
            20                  25                  30

Arg Ala Gly Arg Pro Ile Gly Gly Gly Lys Ser Ser Tyr Ala Arg Lys
        35                  40                  45

Arg Arg Ala Ile Lys Met Gly Arg Cys Val Arg Cys Tyr Arg Val Ser
     50                  55                  60

Pro Pro Phe Tyr His Thr Thr Arg Cys Asp Gly Leu Ser Cys Val Pro
 65                  70                  75                  80

Gly Leu Ser Leu Asn Ala Gly Val Ala Arg Leu Ile Lys Gly Gly Val
                85                  90                  95

Thr Glu Val Ile Pro Ser
            100


<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5

ggaatcagca ttttgggaat                                                  20


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6

atgggatcac ctcagttact                                                  20


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7

tgccacttac accgcctcct                                                  20
```

-continued

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8

gctaccatgg acgtccgcgc ggt                                          23


<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9

cgatggtacc tgcaggcgcg cc                                           22
```